United States Patent
Morgan et al.

(10) Patent No.: US 6,955,073 B2
(45) Date of Patent: Oct. 18, 2005

(54) PRESSURE SENSING IN SURGICAL CONSOLE

(75) Inventors: Michael D. Morgan, Costa Mesa, CA (US); Gary P. Sorensen, Lake Forest, CA (US)

(73) Assignee: Alcon, Inc., Hunenberg (CH)

( * ) Notice: Subject to any disclaimer, the term of this patent is extended or adjusted under 35 U.S.C. 154(b) by 154 days.

(21) Appl. No.: 10/375,959

(22) Filed: Feb. 28, 2003

(65) Prior Publication Data

US 2004/0074282 A1    Apr. 22, 2004

Related U.S. Application Data

(60) Provisional application No. 60/418,737, filed on Oct. 16, 2002.

(51) Int. Cl.[7] .............................................. G01L 27/00
(52) U.S. Cl. ....................................................... 73/1.58
(58) Field of Search ................................ 73/1.58, 1.57, 73/1.66; 604/19, 22, 35, 65, 67, 118, 119, 604/27, 36

(56) References Cited

U.S. PATENT DOCUMENTS

| | | |
|---|---|---|
| 526,917 A | 10/1894 | Cochran |
| 1,718,494 A | 6/1929 | Schurig |
| 2,260,837 A | 10/1941 | Kuehni |
| 2,510,073 A | 6/1950 | Clark |
| 2,583,941 A | 1/1952 | Gordon |
| 3,805,617 A | 4/1974 | Kamazuka |
| 4,192,191 A | 3/1980 | Nelson |
| 4,281,666 A | 8/1981 | Cosman |
| 4,281,667 A | 8/1981 | Cosman |
| 4,452,202 A | 6/1984 | Meyer |
| 4,505,157 A | 3/1985 | Hong Le |
| 4,539,849 A | 9/1985 | Pike |
| 4,541,283 A | 9/1985 | Stuhlmann |
| 4,653,508 A | 3/1987 | Cosman |
| 4,658,829 A * | 4/1987 | Wallace ...................... 600/488 |
| 4,755,669 A | 7/1988 | Grant et al. |
| 4,886,070 A | 12/1989 | Demarest |
| 4,892,985 A | 1/1990 | Tateishi |
| RE33,360 E | 10/1990 | Reynolds et al. |
| RE33,518 E | 1/1991 | McCord et al. |
| 5,029,478 A | 7/1991 | Wamstad |
| 5,080,098 A | 1/1992 | Willett et al. |
| 5,095,401 A | 3/1992 | Zavracky et al. |
| 5,144,843 A | 9/1992 | Tamura et al. |

(Continued)

FOREIGN PATENT DOCUMENTS

| | | |
|---|---|---|
| EP | 0 579 504 | 1/1994 |
| EP | 1 258 717 | 11/2002 |
| WO | WO 88/04042 | 6/1988 |
| WO | WO 93/24817 | 9/1993 |
| WO | WO 00/44415 | 8/2000 |

OTHER PUBLICATIONS

Lebow® Load Cell and Torque Sensor handbook, pp. 63-99 (1989).

*Primary Examiner*—Robert Raevis
(74) *Attorney, Agent, or Firm*—W. David Lee

(57) ABSTRACT

A method of determining the accuracy of a pressure sensor in a surgical console is disclosed. The method involves actuating a linear actuator so that its plunger is linearly displaced a pre-defined amount, and measuring the force exerted by the plunger on a non-compliant member. The accuracy of the linear actuator and the plunger are determined by comparing the force measured in the measuring step to a pre-defined force.

8 Claims, 2 Drawing Sheets

U.S. PATENT DOCUMENTS

| | | |
|---|---|---|
| 5,257,630 A | 11/1993 | Broitman et al. |
| 5,275,053 A | 1/1994 | Wlodarczyk et al. |
| 5,333,504 A | 8/1994 | Lutz et al. |
| 5,353,633 A | 10/1994 | Benedikt et al. |
| 5,392,653 A | 2/1995 | Zanger et al. |
| 5,460,049 A | 10/1995 | Kirsch |
| 5,460,490 A | 10/1995 | Carr et al. |
| 5,470,312 A | 11/1995 | Zanger et al. |
| 5,528,214 A | 6/1996 | Koga et al. |
| 5,583,297 A | 12/1996 | Stocker et al. |
| 5,661,245 A | 8/1997 | Svoboda et al. |
| 5,752,918 A | 5/1998 | Fowler et al. |
| 5,848,971 A | 12/1998 | Fowler et al. |
| 5,866,822 A | 2/1999 | Willig |
| 5,880,373 A | 3/1999 | Barton |
| 5,910,110 A | 6/1999 | Bastable |
| 6,058,779 A | 5/2000 | Cole |
| 6,293,926 B1 | 9/2001 | Sorensen et al. |
| 2001/0004684 A1 | 6/2001 | Morgan et al. |

\* cited by examiner

PRESSURE SENSING IN SURGICAL CONSOLE

This application claims the priority of U.S. Provisional Application No. 60/418,737 filed Oct. 16, 2002.

FIELD OF THE INVENTION

This invention relates generally to pressure sensors used on surgical cassettes and surgical consoles and more particularly to a method of testing the accuracy of such sensors prior to surgery.

DESCRIPTION OF THE RELATED ART

Surgical cassettes utilized in phacoemsulsification, vitreoretinal, or other ophthalmic surgical procedures typically have an aspiration manifold within the cassette. When the cassette is inserted into an ophthalmic surgical console, the aspiration manifold is operatively coupled to a source of vacuum. The cassette is also fluidly coupled to the aspiration port of an ophthalmic surgical handpiece, typically via flexible plastic tubing. Ophthalmic tissue is aspirated by the handpiece into a collection bag that is also fluidly coupled to the aspiration manifold of the cassette. Such cassettes typically employ a variety of pressure sensors to measure the vacuum level within the aspiration manifold of the cassette and thus the eye. For example, such cassettes have utilized both conventional vacuum transducers and non-invasive pressure sensors to measure such vacuum. Exemplary non-invasive pressure sensors are disclosed in U.S. Pat. Nos. 5,910,110 to Bastable and 5,470,312 to Zanger et al., both of which are incorporated herein in their entirety by reference.

Communicating an accurate reading of the vacuum level within the aspiration manifold of such surgical cassettes to the surgeon is critical to the success of the surgical procedure and the safety of the patient. For example, during a phacoemulsification procedure, the tip of the phacoemulsification handpiece may become occluded with ophthalmic tissue. When the tip occludes, the peristaltic pump vacuum source of the surgical system continues to pump, increasing the vacuum within the aspiration line of the handpiece. When the blockage on the tip is removed, the patient's eye may be exposed to a dangerous surge of vacuum. However, if the vacuum level within the aspiration manifold of the cassette is measured and provided to the surgeon, the surgeon can use the user interface of the surgical console to slow down or stop the peristaltic pump to bring the vacuum to the desired level before the blockage breaks free. To insure that an accurate aspiration manifold vacuum reading is provided to the surgeon, certain ophthalmic surgical systems utilize two pressure sensors to measure vacuum in the aspiration manifold of the cassette. With this design, the surgeon still receives an accurate measurement of the vacuum level within the aspiration manifold of the cassette even if one of the sensors fails or is not working properly. However, such dual redundancy increases the cost and complexity of the surgical system and cassette. Therefore, a need exists for an improved apparatus and method of insuring the accuracy of such pressure sensors.

SUMMARY OF THE INVENTION

The present invention is directed to a method of determining the accuracy of a pressure sensor in a surgical console. A substantially non-compliant member is provided. A surgical console with a cassette receiving area and a linear actuator having a plunger are also provided. The substantially con-compliant member is disposed in the cassette receiving area. The linear actuator is actuated so that the plunger is linearly displaced a pre-defined amount, and the force exerted by the plunger on the non-compliant member is measured. The accuracy of the linear actuator and the plunger are determined by comparing the force measured in the measuring step to a pre-defined force.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1–6 of the drawings, like numerals being used for like and corresponding parts of the various drawings.

Figure 1:
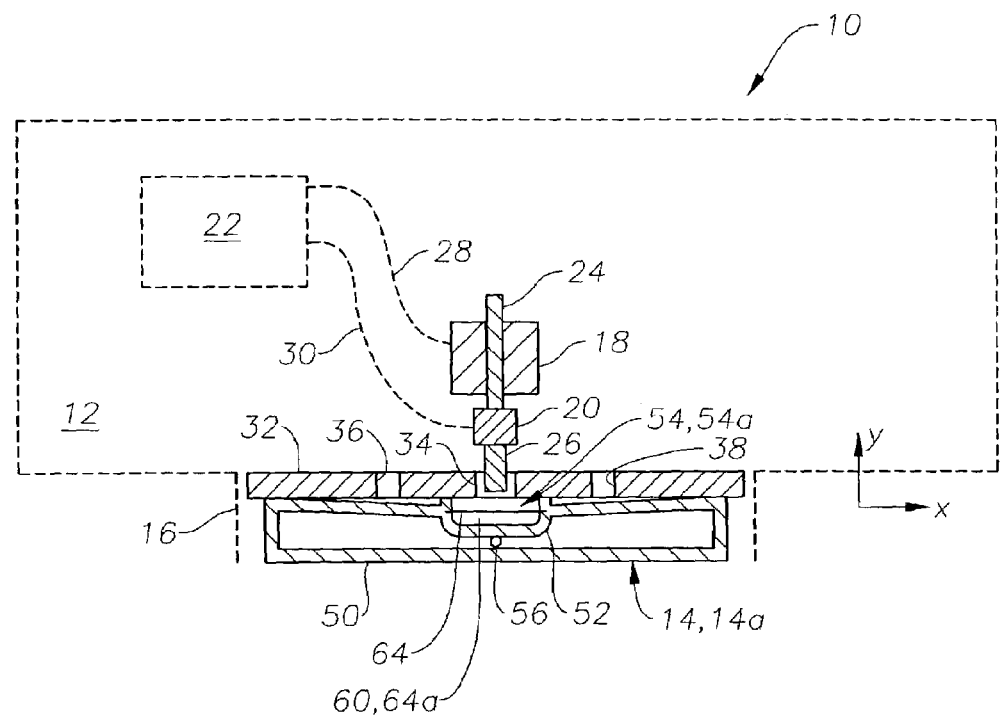
FIG. 1 is a top, partially sectional view schematically illustrating the relevant portions of a surgical system and cassette according to a preferred embodiment of the present invention.
Figure 2:
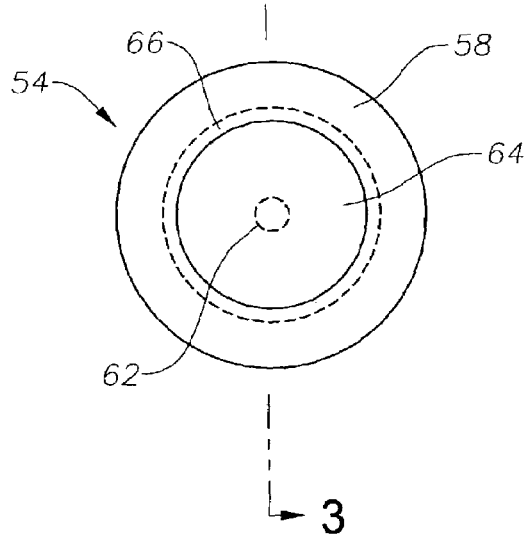
FIG. 2 is a front view of the non-invasive pressure sensor of the surgical cassette of FIG. 1 according to a preferred embodiment of the present invention.
Figure 3:
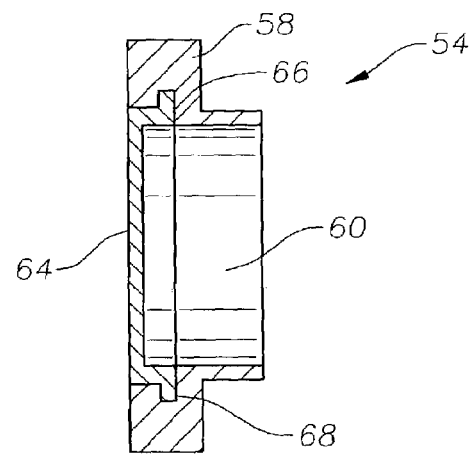
FIG. 3 is a side, sectional view of the sensor of FIG. 2 along line 3—3.

Referring to FIGS. 1–3, a surgical system 10 generally includes a surgical console 12 and a surgical cassette 14. Console 12 and cassette 14 are preferably for use in ophthalmic surgery, although the present invention is applicable to other surgical systems that provide aspiration to a surgical handpiece. Surgical console 12 includes a cassette receiving area 16 for removably receiving cassette 14, a linear actuator 18, a load cell or force gage 20, and a computer or microprocessor 22. Linear actuator 18 includes a lead screw 24 having a plunger 26 on one end. Linear actuator 18 is preferably a conventional linear stepper motor having a shaft 24. A preferred linear stepper motor 18 is the Model ZB17 GBKR-13 available from Eastern Air Devices (EAD) of Dover, N.H. The rotation of linear stepper motor 18 one step preferably results in a 0.0003125 inch linear displacement of shaft 24 and plunger 26. However, linear actuator 18 may also be a DC motor with position feedback, a pneumatically actuated piston, or other conventional means of moving a plunger with a known displacement. A preferred load cell for load cell 20 is the Model 31 available from Sensotec of Columbus, Ohio. Linear stepper motor 18 and load cell 20 are electronically coupled to computer 22 in a conventional manner, as schematically illustrated by lines 28 and 30, respectively. Cassette receiving area 16 has a front plate 32 for interfacing with cassette 14 including an aperture 34 for plunger 26 and apertures 36 and 38 for other plungers of console 12 used to interface with various portions of cassette 14.

Surgical cassette 14 generally includes a body 50 having a pressure sensor receiving area 52, a non-invasive pressure sensor 54 disposed in receiving area 52, and an aspiration manifold 56 fluidly coupled to sensor 54. Body 50 is preferably a rigid thermoplastic and may be made from any suitable method, such as machining or injection molding. Although not shown if the Figures, cassette 14 may also include additional fluid channels, manifolds, or ports that provide control of aspiration or irrigation fluid. A preferred ophthalmic surgical cassette for cassette 14 is disclosed in U.S. Pat. No. 6,293,926, which is incorporated herein in its entirety by this reference.

Pressure sensor 54 has a body 58 having a cavity 60, a port 62 for fluidly coupling with aspiration manifold 56, and a diaphragm or membrane 64. Body 58 is preferably a rigid thermoplastic, and diaphragm 64 is preferably made of stainless steel. Diaphragm 64 has a rim 66 that mates with a recess 68 in body 58 to retain diaphragm 64 within body 58. Diaphragm 64 preferably has a diameter of about 0.996 inches (not including rim 66). Diaphragm 64 preferably has a thickness of about 0.0027 inches to about 0.0033 inches, and most preferably about 0.003 inches. Diaphragm 64 is preferably made of 17-7 stainless steel.

Figure 4:
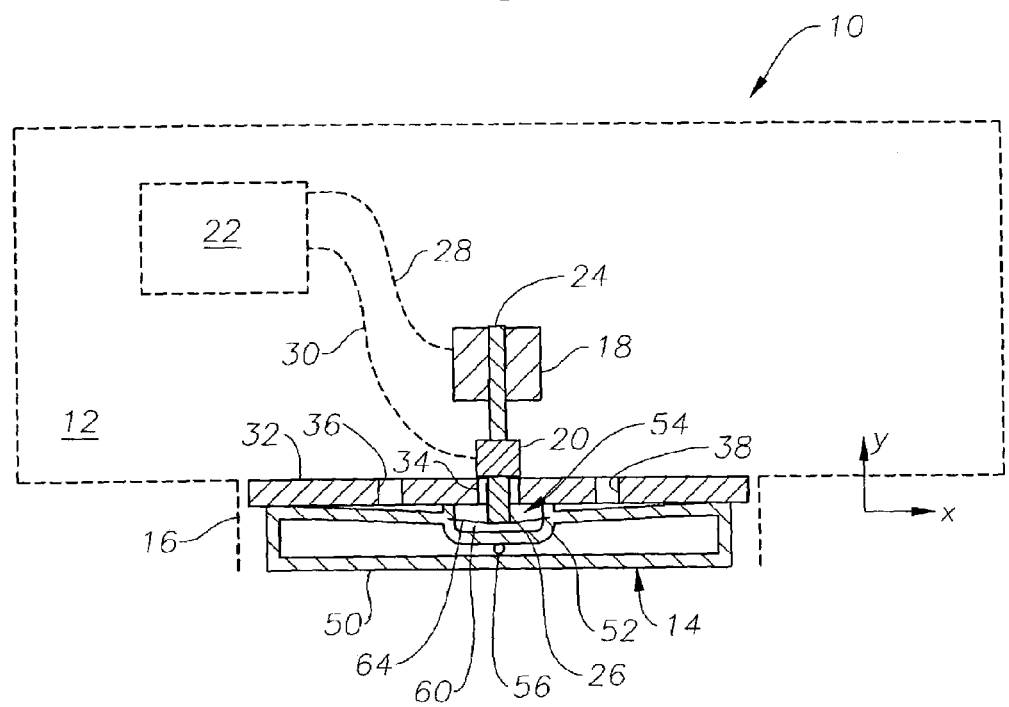
FIG. 4 is a top, partially sectional view similar to FIG. 1 showing the plunger of the surgical system loading the diaphragm of the sensor of FIGS. 2–3.
Figure 5:
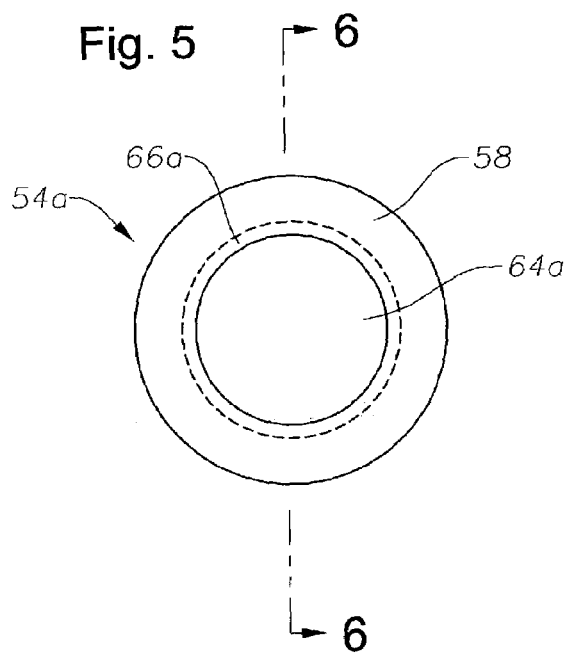
FIG. 5 is front view of the non-invasive pressure sensor of FIGS. 2–3 having a non-compliant member instead of a diaphragm.
Figure 6:
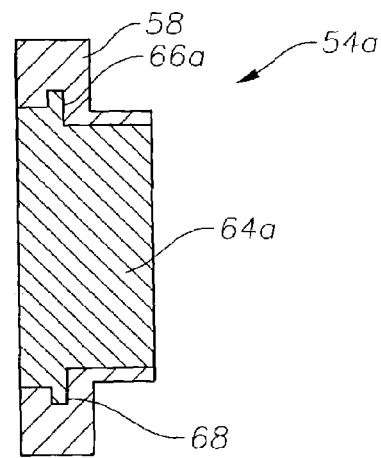
FIG. 6 is a side, sectional view of the sensor of FIG. 5 along line 6—6.

When cassette 14 is inserted into cassette receiving area 16 of console 12, computer 22 rotates stepper motor 18, causing shaft 24 and plunger 26 to be moved linearly through aperture 34 toward diaphragm 64 of sensor 54. Stepper motor 18 moves plunger 26 until it contacts and displaces diaphragm 64, as shown in FIG. 4. Plunger 26 preferably displaces diaphragm 64 until a known pre-load force ("$F_{preload}$") is placed on diaphragm 64 as measured by load cell 20. $F_{preload}$ must be greater than the largest vacuum exerted on diaphragm 64 via aspiration manifold 56 of cassette 14 and cavity 60 of sensor 54. $F_{preload}$ for diaphragm 64 is preferably about 4.0 $lb_f$.

When console 12 provides vacuum to aspiration manifold 56 of cassette 14 and thus cavity 60 of sensor 54, the absolute value of the force exerted on diaphragm 64 by plunger 26 varies in an inversely proportional manner with the absolute value of the vacuum level. In other words, larger absolute values of vacuum yield smaller absolute values of force exerted by plunger 64, and smaller absolute values of vacuum yield larger absolute values of force exerted by plunger 64. This relationship may be calibrated so that when load cell 20 provides a force measurement to computer 22, computer 22 can calculate the vacuum level within cavity 60, aspiration manifold 56, and the eye.

It is critical that linear stepper motor 18, shaft 24, plunger 26, and sensor 54 cooperate together to accurately measure the vacuum within aspiration manifold 56 of cassette 14. A preferred method of testing the accuracy of sensor 54 is disclosed in U.S. Pat. No. 6,868,720, which is incorporated herein in its entirety by reference. In addition, it has been discovered that periodic testing of stepper motor 18, shaft 24, and plunger 26 is desired to insure accurate pressure sensing by this system. Such testing can be initiated when desired by the user via the user interface of surgical console 12 in conjunction with a test cassette 14a. Computer 22 may also signal the surgeon that such testing is desired based upon a pre-defined number of insertions of cassette 14 into cassette receiving area 16.

The following describes the preferred procedure for testing the accuracy of linear stepper motor 18, shaft 24, and plunger 26. A test cassette 14a is inserted into cassette receiving area 16 of console 12, as shown in FIG. 1. Cassette 14a is preferably identical to cassette 14, except that it has a pressure sensor 54a with a hardened steel plate 64a (see FIGS. 5–6), or other substantially non-compliant member, disposed in pressure sensor receiving area 52 instead of pressure sensor 54. Computer 22 rotates linear stepper motor 18 so that load cell 20 just begins to provide a measurement to computer 22 of the force exerted by plunger 26 against non-compliant member 64a ("$F_{plunger}$"). Computer 22 then rotates linear stepper motor 18 back 1 step. This plunger displacement is defined as "$D_0$". The linear displacement of plunger 26 beyond $D_0$ is a function of the rotation of linear stepper motor 18 and is defined as "D". Computer 22 then rotates linear stepper motor 18 in a step by step fashion until $F_{plunger}$ equals a pre-defined maximum force (preferably $F_{preload}$). Load cell 20 measures $F_{plunger}$ for each step and provides this force to computer 22. Computer 22 stores the value of D and the associated value of $F_{plunger}$ for each step. Computer 22 also compares the measured value of $F_{plunger}$ to the desired value of $F_{plunger}$ for each value of D. If the measured value of $F_{plunger}$ is not within a pre-defined tolerance of the desired value of $F_{plunger}$, computer 22 signals the user via console 12 that the pressure sensing of console 12 is in need of repair. Computer 22 may also prevent any surgical procedure due to the defective pressure sensing. If the measured value of $F_{plunger}$ is within the pre-defined tolerance of the desired value of $F_{plunger}$ for all values of D, then linear stepper motor 18, shaft 24, and plunger 26 are measuring accurately.

From the above, it may be appreciated that the present invention provides a simple and reliable apparatus and method of insuring the accuracy of a non-invasive pressure sensor of a surgical cassette. The present invention is illustrated herein by example, and various modifications may be made by a person of ordinary skill in the art. For example, the present invention may be implemented with other linear actuators other than linear stepper motor 18 such as a DC motor with position feedback, a pneumatically actuated piston, or other conventional means of moving a plunger with a known displacement. As another example, a substantially non-compliant member may be disposed in pressure sensor receiving area 52 without the additional structure of pressure sensor 54a. As a further example, a substantially non-compliant member may be inserted into cassette receiving area 16 instead of surgical cassette 14a having pressure sensor 54a with substantially non-compliant member 64a. As a further example, computer 22 may generate a force $F_{plunger}$ versus displacement D curve for a given console 12 and substantially non-compliant member for the entire range of values of D, and then compare this curve to a "tolerance" curve in a batch mode rather than comparing each measured value of $F_{plunger}$ to see if it is within the pre-defined tolerance at the time its measured, as described above. As a further example, $F_{plunger}$ may be measured at intervals of a pre-defined number of steps of linear stepper motor 18 instead of at each step of linear stepper motor 18 as described above. As a further example, computer 22 may monitor the number of steps of linear stepper motor 18 required for $F_{plunger}$ to equal a pre-defined force and have console 12 signal the user, or prevent any surgical procedure, if the monitored number of steps does not equal a pre-defined number of steps for the pre-defined force.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of determining the accuracy of a pressure sensor in a surgical console, comprising the steps of:
providing a substantially non-compliant member;
providing a surgical console with a cassette receiving area and a linear actuator having a plunger;
disposing said substantially non-compliant member in said cassette receiving area;
actuating said linear actuator so that said plunger exerts a force on said substantially non-compliant member;
measuring said force exerted by said plunger on said substantially non-compliant member; and
determining an accuracy of said linear actuator and said plunger by comparing said force measured in said measuring step to a pre-defined force.

2. The method of claim 1 further comprising the step of providing information to a user of said surgical console when said force measured in said measuring step is not within a pre-defined tolerance of said pre-defined force.

3. The method of claim 1 further comprising the step of preventing a surgical procedure when said force measured in said measuring step is not within a pre-defined tolerance of said pre-defined force.

4. The method of claim 1 wherein:
said surgical console comprises a load cell operatively coupled to said plunger; and
said measuring step comprises measuring said force exerted by said plunger on said substantially non-compliant member with said load cell.

5. A method of determining the accuracy of a pressure sensor in a surgical console, comprising the steps of:
providing a surgical cassette having a pressure sensor receiving area and a substantially non-compliant member disposed in said pressure sensor receiving area;
providing a surgical console with a cassette receiving area and linear stepper motor having a plunger;
disposing said cassette in said cassette receiving area;
actuating said linear stepper motor a pre-defined number of steps so that said plunger exerts a force on said substantially non-compliant member;
measuring said force exerted by said plunger on said substantially non-compliant member;
determining an accuracy of said linear stepper motor and said plunger by comparing said force measured in said measuring step to a pre-defined force.

6. The method of claim 5 further comprising the step of providing information to a user of said surgical console when said force measured in said measuring step is not within a pre-defined tolerance of said pre-defined force.

7. The method of claim 5 further comprising the step of preventing a surgical procedure when said force measured in said measuring step is not within a pre-defined tolerance of said pre-defined force.

8. The method of claim 5 wherein:
said surgical console comprises a load cell operatively coupled to said plunger; and
said measuring step comprises measuring said force exerted by said plunger on said substantially non-compliant member with said load cell.

* * * * *